United States Patent [19]

Hayes et al.

[11] Patent Number: 4,500,466

[45] Date of Patent: Feb. 19, 1985

[54] METHOD FOR PREPARING A ZINC DIMETHACRYLATE POWDER HAVING A SPECIFIC SURFACE AREA RANGE

[75] Inventors: Robert A. Hayes, Cuyahoga Falls; Wendell R. Conard, Kent, both of Ohio

[73] Assignee: The Firestone Tire & Rubber Company, Akron, Ohio

[21] Appl. No.: 543,705

[22] Filed: Oct. 20, 1983

Related U.S. Application Data

[63] Continuation-in-part of Ser. No. 421,012, Sep. 21, 1982, abandoned.

[51] Int. Cl.³ .................. C07F 3/06; C08K 3/04; C08L 7/00; C08F 275/00
[52] U.S. Cl. .................. 260/429.9; 525/273; 525/274; 524/496; 524/533; 524/535
[58] Field of Search ............ 260/429.9; 525/274, 525/273

[56] References Cited

U.S. PATENT DOCUMENTS 4,100,182  7/1978  Martin et al. ............ 260/429.9
4,305,881  12/1981  Tominaga ............ 260/5

FOREIGN PATENT DOCUMENTS 138616  11/1976  Japan

OTHER PUBLICATIONS

Derwent Abst. 84518 E/40 Sumitomo (8-1982).
Chem. Abst. 87-5403 (1977) Kobayashi et al. (J76-138616).
Chem. Abst. 98-88828(h)-1983 Sumitomo 82JP-139034.
Derwent Abst. 04528 Y/03 (11-1976) Nippon.

*Primary Examiner*—Herbert J. Lilling
*Attorney, Agent, or Firm*—Frank J. Troy, Sr.

[57] ABSTRACT

Vulcanizable polymeric compositions comprising certain rubbery polymers or polymer blends, a zinc dimethacrylate adjuvant having a surface area of from about 3.7 to about 5.4 $m^2/g$ or more and a peroxide curing agent are provided. Polymeric compositions which contain 25 parts by weight or more of the zinc dimethacrylate adjuvant per 100 parts by weight of rubbery polymer in the absence of reinforcing fillers exhibit excellent strength and hysteresis characteristics when cured. The surface area of the zinc dimethacrylate adjuvant along with its method of preparation are extremely important factors in the excellent properties obtained when polymeric compositions containing the adjuvant are cured.

6 Claims, No Drawings

METHOD FOR PREPARING A ZINC DIMETHACRYLATE POWDER HAVING A SPECIFIC SURFACE AREA RANGE

CROSS REFERENCES TO RELATED APPLICATIONS

This is a continuation-in-part of U.S. application Ser. No. 421,012, filed Sept. 21, 1982 and now abandoned.

BACKGROUND OF THE INVENTION

The invention relates to vulcanizable polymeric compositions containing a zinc dimethacrylate adjuvant and to a method of preparing the adjuvant. More particularly, the invention relates to vulcanizable polymeric compositions comprising certain rubbery polymers or polymer blends, a zinc dimethacrylate adjuvant having specified surface area limitations and peroxide curing agents, and to a method of preparing the zinc dimethacrylate.

Various patents and publications describe the preparation of metallic salts of methacrylic acid.

Thus, Japan Kokai No. 76,138,616 relates to the preparation of zinc dimethacrylate and zinc diacrylate by a process which involves reacting acrylic or methacrylic acid with zinc oxide or zinc hydroxide at 40°-100° C. in water insoluble hydrocarbon solvent mixtures in which the hydrocarbon solvent forms an azeotrope with water, removing the water by azeotropic distillation and drying the resultant product. Hydrocarbon solvents which are disclosed include benzene, toluene, xylenes, cyclohexane, methylcyclohexane, n-heptane, n-hexane, etc.

U.S. Pat. No. 4,082,288 relates to the preparation of basic zinc methacrylate by milling under agitation methacrylic acid with a suspension of zinc oxide in a liquid medium such as water or a volatile organic liquid.

U.S. Pat. No. 4,100,182 relates to a method for preparing an adjuvant for an elastomeric composition which involves mixing methacrylic acid with zinc oxide in a liquid medium in the proportions required to form basic zinc methacrylate, removing the liquid medium and finely dividing the resulting reaction product. The reference teaches that the molar ratios of zinc oxide to methacrylic acid used in forming the reaction product is ordinarily at least 0.8 to 1, preferably 2 to 1 (column 2 lines 18-30); that the liquid medium may be water or a volatile organic liquid such as a hydrocarbon liquid or an alkanol (column 2 lines 45-48) and that the reaction product should be finely powdered to at least a fineness sufficient to pass a 200 mesh sieve preferably a 300 mesh sieve.

U.S. Pat. No. 4,191,671 apparently discloses the in-situ preparation of zinc methacrylate by a process which involves first mixing a rubbery polymer such as polybutadiene with methacrylic acid, then adding zinc oxide thereto in a standard kneader and mixing to obtain a homogeneous rubber composition.

U.S. Pat. No. 4,266,772 discloses the preparation of basic zinc methacrylate using the same process described in U.S. Pat. No. 4,082,288. The article entitled "Elastic Properties and Structures of Polybutadiene Vulcanized With Magnesium Methacrylate" appearing in the Journal of Applied Polymer Science, Vol. 16, pages 505-518 (1972) at page 505 states magnesium methacrylate utilized therein was prepared by heating aqueous solutions of the acid and magnesium hydroxide and then passing the salt through a sieve to obtain salt particles having a diameter of less than 0.5 millimeters.

In addition, various patents and publications describe vulcanizable polymeric compositions containing metallic salts of methacrylic acid.

Thus, U.S. Pat. No. 3,823,122 relates to curable SBR or neoprene elastomer compositions containing from 1 to 15 parts by weight per 100 parts by weight of elastomer of a substituted acrylic acid or acid salt, with the preferred acid salt indicated to be zinc methacrylate which is described as being formed by merely reacting sodium methacrylate with zinc chloride. Elastomer compositions which are disclosed include a reinforcing filler such as carbon black but do not include a peroxide curing agent.

U.S. Pat. No. 4,082,288 discloses free-radial crosslinkable elastomer compositions containing a peroxide crosslinkable elastomer, from 10 to about 60 parts by weight per 100 parts by weight of elastomer of basic zinc methacrylate, a peroxide curing agent and optionally reinforcing fillers such as litharge or zinc oxide in amounts of 2 to 10 parts by weight per 100 parts by weight of elastomer.

U.S. Pat. No. 4,191,671 relates to curable rubber compositions comprising (A) a diene elastomer, (B) an alphabeta ethylenically unsaturated carboxylic acid, wherein the ratio by weight of component (A) to component (B) is 87/13 to 55/45, (C) a divalent metal compound being present in quantities of 50 to 150 parts by weight per 100 parts by weight of component (B), and (D) an organic peroxide being present in quantities of 0.3 to 5.0 parts by weight per 100 parts by weight of the combined weight of components (A) and (B). The compositions may additionally contain an unpolymerizable carboxylic acid, carbon black in amounts of less than 50 parts by weight per 100 parts by weight of elastomer and an amine and/or phenol compound.

U.S. Pat. No. 4,192,790 relates to elastomer compositions having reduced Mooney viscosity in the compounded state. The Mooney viscosity of the elastomer compositions are reduced by the incorporation therein of from 0.1 to 7.0 parts by weight of basic zinc methacrylate per 100 parts by weight of elastomer. In addition to the basic zinc methacrylate, the elastomer compositions contain various elastomers or elastomer blends, an inorganic particulate filler and optionally carbon black (20 to 150 parts per 100 parts elastomer) and curing agents such as peroxide curatives.

U.S. Pat. No. 4,266,772 relates to solid golf balls formed from a curable elastomer composition comprising a freeradical crosslinkable elastomer, especially a peroxide crosslinkable elastomer, basic zinc methacrylate (about 10 to about 60 parts by weight per 100 parts by weight of elastomer) and a curing agent such as a peroxide curing agent. The compositions may optionally contain reinforcing fillers such as litharge or zinc oxide in amounts of for example 2 to 10 parts per 100 parts of elastomer.

British Pat. No. 1,091,818 discloses vulcanizable compositions comprising alpha-olefin polymers and a curing system consisting of metal salts of acrylic acid or methacrylic acid in amounts of from 1 to 10 parts of metal salt per 100 parts of polymer and an organic peroxide. The compositions may additionally contain reinforcing agents and fillers such as carbon blacks, metal oxides, etc.

British Pat. No. 2,042,553 discloses crosslinked cellular elastomeric compositions which are formed from an elastomer composition comprising a natural and/or synthetic rubber, a crosslinking agent such as a peroxide, a monomeric metallic salt such as zinc dimethacrylate, zinc diacrylate, preferably basic zinc methacrylate and a blowing agent. The compositions may additionally contain fillers such as carbon black or titanium dioxide and other known compounding additives.

The article entitled "Vulcanization of Rubbers By Salts of Unsaturated Acids. Vulcanization of Butadiene-Styrene Rubber By Methacrylate Salts" by A. A. Dontsov et al. appearing in the Colloid Journal USSR, Volume 31, pages 293-297 (1969) discloses vulcanizable compositions comprising butadiene-styrene rubber or ethylene-propylene rubber, magnesium methacrylate or sodium methacrylate and dicumyl peroxide.

The article entitled "Elastic Properties and Structure of Polybutadiene Vulcanized with Magnesium Methacrylate" by A. Dontsov et al. appearing in the Journal of Applied Polymer Science, Volume 16, pages 505-518 (1972) discloses vulcanizable compositions comprising polybutadiene, magnesium methacrylate and dicumyl peroxide.

The article entitled "General Regularities of Heterogeneous Vulcanization" by A. A. Dontsov appearing in the publication Rubbercon '77, International Rubber Conference, Volume 2, pages 26-1 through 26-12 (1977) discloses vulcanizable compositions comprising styrene-butadiene rubber or ethylene-propylene rubber; magnesium, sodium, zinc and cadmium salts of methacrylic, maleic and betaphenyl acrylic acids and radical type initiators such as dicumyl peroxide.

SUMMARY OF THE INVENTION

In accordance with one embodiment of the invention, a method for preparing a zinc dimethacrylate powder having a surface area of from about 3.7 to about 5.4 $m^2/g$ or more is provided. The method generally involves first reacting under agitation zinc oxide and methacrylic acid in an amount of from about 0.5 to about 0.6 moles of zinc oxide per mole of methacrylic acid in a liquid aliphatic hydrocarbon dispersing medium to produce particles of zinc dimethacrylate in the liquid medium. Then, the particles of zinc dimethacrylate are recovered from the liquid medium and dried to produce the zinc dimethacrylate powder.

In a further embodiment of the invention, vulcanizable polymeric compositions are provided which comprise (a) rubbery polymers selected from the group consisting of natural rubber, ethylene/propylene copolymers, ethylene/propylene/diene terpolymers, styrene/butadiene copolymers, nitrile rubbers, neoprene and blends thereof; (b) from about 25 to about 85 parts by weight per 100 parts by weight of said rubbery polymers of said zinc dimethacrylate having a surface area of from about 3.7 to about 5.4 $m^2/g$ or more; and (c) a cure effective amount of a peroxide curing agent. Such polymeric compositions exhibit excellent strength and hysteresis characteristics in the cured state.

DETAILED DESCRIPTION OF THE INVENTION

To prepare the zinc dimethacrylate powder, the zinc oxide and methacrylic acid are first brought together in a liquid aliphatic hydrocarbon disperson medium which aids in dissipating the heat that is liberated by the exothermic reaction of the two materials. Preferably, the zinc oxide is first dispersed in the liquid medium and the methacrylic acid is then added to the dispersion while agitating. From about 0.5 to about 0.6 moles of zinc oxide per mole of methacrylic acid are employed in the reaction.

Various liquid aliphatic hydrocarbons may be utilized as the liquid dispersion medium. However, it is preferred to utilize an alkane as the liquid dispersion medium and of the alkanes, hexane is especially preferred. A surprising aspect of the use of hexane as the dispersion medium is the finding that the zinc dimethacrylate powder produced by reaction in the hexane medium consistently exhibits the desired surface area characteristics even under varying conditions of agitation.

While not essential, it is generally preferred to include a small amount of a nonionic surfactant in the dispersion medium as this aids in producing a fluid suspension which is pumpable and pourable. Various well known nonionic surfactants can be utilized for that purpose including silicone type surfactants and alkylaryl polyether alcohol types. Preferred nonionic surfactants are the alkylaryl polyether alcohols.

Amounts of nonionic surfactant included in the dispersion medium may range from about 0.1 to about 1.0%, preferably 0.3 to 0.5% by weight based on the combined weight of zinc oxide and methacrylic acid.

The reaction between the zinc oxide and methacrylic acid is preferably conducted at room or ambient temperature (i.e., no added heat), under agitation and in the presence of the nonionic surfactant. This preferred reaction procedure produces a fluid suspension which as indicated above is both pumpable and pourable. If desired, the reaction can be conducted at temperatures of up to about 70° C. and without a surfactant. In this latter case, a slurry or thick paste is obtained which does not pour well. However, this procedure though not preferred, does not appear to degrade the finished product.

Reaction times may vary considerably depending on factors such as batch size, degree of agitation and the like. In general, reaction times may range from about 4 to about 20 hours or more.

In the preferred embodiment, as the reaction between the zinc oxide and methacrylic acid nears completion, the product takes on the form of a fluid suspension of zinc dimethacrylate particles in the liquid medium, whereas when the reaction is conducted at higher temperatures and without surfactant, the product takes on the form of a slurry of zinc dimethacrylate particles in the liquid medium.

In any event, the second step in the method is to recover the particles of zinc dimethacrylate from the liquid medium. This can be accomplished by any convenient method. Thus, for example, the zinc dimethacrylate particles may be recovered by filtration (which is preferred) or by removal of the liquid medium as by evaporation. When the zinc dimethacrylate particles are recovered by filtration, it is often desirable and preferred to remove additional portions of the liquid medium by pressing the particles.

Following the recovery step, the zinc dimethacrylate particles are dried to produce the zinc dimethacrylate powder. Drying can be accomplished by any conventional method. Thus, air drying and/or vacuum drying can be utilized. It is often preferred to first air dry the particles and then vacuum dry in an oven at temperatures of from about 60° C. to about 70° C.

The zinc dimethacrylate product at this point is in the form of a lightly caked powder. If desired, the product can be used in that form as an adjuvant in compositions of the invention with good results. However, it is generally preferred to break up the lightly caked powder for ease of handling and blending with the rubbery polymers and other components to prepare the compositions of the invention. This can be accomplished in any known manner. Thus, for example, the lightly caked powder can be broken up by a suitable blender such as a Waring blender. While not essential, it is usually desirable and preferred to remove any exceptionally large particles from the powder by passing the powder through an appropriate sieve such as, for example, a number 50 mesh screen.

The zinc dimethacrylate product prepared in accordance with the above process generally has an ash content of from about 30 to about 35 percent.

Rubbery polymers which may be utilized as component (a) in the compositions of the invention include natural rubber; ehtylene/propylene copolymers; ethylene/propylene/diene terpolymers in which the diene component is a nonconjugated diene such as 1,4-hexadiene, dicyclopentadiene, 5-ethylidene-2-norbornene and the like; styrene/butadiene copolymers (i.e., SBR), nitrile rubber, neoprene and blends or mixtures thereof.

One of the surprising and unexpected aspects of the composition of the invention has been the discovery that the use of the zinc dimethacrylate and peroxide components permits the cure of rubbery polymer blends which are normally regarded as "cure incompatible." For example, it has been found that compositions containing blends of EPDM and nitrile rubber cure well and exhibit excellent strength.

Another surprising aspect of the compositions of the invention is the discovery that compositions containing ethylene/propylene rubber which contains no unsaturation also cure well and exhibit good strength characteristics.

The zinc dimethacrylate utilized as component (b) of the composition is as indicated a zinc dimethacrylate powder having a surface area of from about 3.7 to about 5.4 square meters per gram ($m^2/g$) or more and an ash content of from about 30 to about 35 percent. The zinc dimethacrylate is prepared in accordance with the process described above.

Amounts of zinc dimethacrylate employed may range from about 25 to about 85 parts by weight per 100 parts by weight of rubbery polymers with preferred amounts being from about 50 to about 80 parts by weight per 100 parts by weight of rubbery polymers. Compositions containing 25 parts by weight of zinc dimethacrylate or more when cured exhibit much lower hysteresis than conventional carbon black reinforced rubbers. Compositions containing 50 parts by weight of zinc dimethacrylate or more when cured exhibit excellent strength characteristics (e.g., modulus, elongation and break strengths) approaching the properties of high quality polyurethanes.

Peroxide curing agents which may be used as component (c) include organic peroxides such as dicumyl peroxide, bis-(t-butyl peroxy)diisopropyl benzene, t-butyl perbenzoate, di-t-butyl peroxide, 2,5-dimethyl-2,5-di-t-butyl peroxy-hexane and the like. The preferred peroxide curing agents are bis-(t-butyl peroxy)diisopropyl benzene and dicumyl peroxide.

Amounts of peroxide curing agents included in the compositions will depend upon the type rubber utilized and may generally be stated as cure effective amounts. In general, such amounts may range from about 0.2 to about 2.0 parts by weight per 100 parts by weight of rubbery polymer.

The compositions may optionally contain other conventional additives which are commonly utilized in rubber compositions. Such additives may include reinforcing agents and fillers such as carbon blacks, clays, silicas and calcium carbonate, process and extender oils, antioxidants, waxes, placticizers and the like. When it is desired to include such reinforcing agents and fillers in the compositions, these may generally be utilized in amounts of from about 5 to about 60 parts by weight per 100 parts by weight of rubber polymers. Other additives may be employed in amounts conventionally used in standard rubber compounds.

The rubber compositions may be prepared by any conventional procedure such as, for example, by mixing the ingredients in an internal mixer or on a mill.

The following examples are submitted for the purpose of further illustrating the nature of the present invention and are not intended as a limitation on the scope thereof. Parts and percentages referred to in the examples and throughout the specification are by weight unless otherwise indicated.

The following examples (i.e., 1-5) illustrate the preparation of zinc dimethacrylate by the process of the invention.

EXAMPLE 1

To each of fifteen (15) 28-ounce beverage bottles were charged 300 grams of hexane. Then 37.5 grams of zinc oxide, previously passed through a number 50 mesh screen were added to the bottles with swirling. Following this addition, 77.5 grams of methacrylic acid were added to each bottle with continued swirling. The bottles were swirled and shaken every 1-2 minutes for 15 minutes. The contents gradually thickened. The bottles were then purged with nitrogen, capped and placed in a 50° C. polymerizer for approximately 2.5 days.

The bottles were then removed from the polymerizer, cooled in water and opened. Following this procedure, the contents of the bottles were blown into a five gallon kettle with nitrogen. The contents of the kettle were then diluted with one gallon of hexane and stirred for 30 minutes. The resultant slurry was filtered in 5 portions each washed with 700 cc of hexane. The filter cakes were then placed in two large trays, broken up by hand and dried in a hood for 3 hours with frequent stirring. The trays were then placed in a vacuum oven operating at a temperature of 65° C. and at 0.01 to 0.05 mm Hg for 40 hours. The resultant zinc dimethacrylate in the form of a lightly caked powder was then broken up in a Waring blender and passed through a 50 mesh screen. Yield of product was 1525.5 grams.

Analysis of the product for ash content showed it to contain 33.7% ash which compares to a theoretical ash content of 34.5%. The product was also subjected to differential thermal analysis (DTA). Procedures for obtaining DTA curves are well known and are described in instrument manufacturers' manuals and various texts. DTA of the product revealed a major endotherm peaking at 177° C. and a minor endotherm peaking at 141° C.

EXAMPLE 2

To a 2-liter three-necked flask equipped with a stirrer, thermometer, nitrogen inlet and outlet was charged 792.0 grams of hexane, 99.0 grams of zinc oxide, 0.3 grams of Ucar Super Wetter FP, a nonionic organo silicone surfactant available from Union Carbide, 0.3 grams of L-522, a nonionic organo silicone surfactant also avilable from Union Carbide and 0.3 grams of DC190, a silicone glycol copolymer surfactant available from Dow Corning Corporation. The contents of the flask were stirred at 250-300 RPM for 23 hours. Then, 204.6 grams of methacrylic acid was added to the flask with stirring continued. Prior to this addition, the contents of the flask were at room temperature (i.e., 27° C.). However, within one minute after addition of the methacrylic acid, an exotherm occurred which caused the temperature to rise to 42° C. The temperature of the reaction mixture slowly dropped reaching a temperature of 35° C. after 30 minutes. The reaction was continued with stirring for a total of 18 hours. The resultant fluid suspension was filtered to recover the zinc dimethacrylate particles; the particles were then washed with hexane, resuspended in 600 cc of hexane, filtered again and washed with hexane. The filter cakes were then placed in trays, dried in a hood and vacuum dried using substantially the same procedure set forth in Example 1. The resultant zinc dimethacrylate in the form of a soft powder was then passed through a 50 mesh screen.

The product was analyzed for ash content and found to contain 34.36% ash which compares to a theoretical ash content of 34.5%.

EXAMPLE 3

To a 5-gallon openhead bucket equipped with a polypropylene liner, baffles placed between the liner and bucket, a high speed air motor with attached stirrer and thermometer was charged in sequence 12,000 cc of hexane, 3.44 cc of Triton X-15, 3.4 cc of Triton X-45, 3.4 cc of Triton X-100, 1008 grams of zinc oxide and 2062 grams of methacrylic acid. (Triton X-15, X-45 and X-100 are nonionic octylphenoxy polyethoxy ethanol surfactants available from Rohm & Haas Company). Following addition of the methacrylic acid, a polyethylene cover was placed over the bucket to prevent loss of hexane by evaporation. The ingredients were added with vigorous stirring. Prior to the addition of methacrylic acid, the temperature inside the bucket was 27° C. (i.e., room temperature). Within two minutes following the addition, an exotherm occurred which caused the temperature to rise to 44° C. The contents of the bucket were vigorously stirred for 8 hours at which time the temperature had dropped to 40° C. The degree of stirring was reduced slightly and the reaction continued for an additional 15 hours (total reaction time 23 hours) at which time the temperature had fallen to 36° C. As the reaction neared completion, the contents in the bucket took on the form of a fluid suspension. The suspension was then removed from the bucket, filtered, and the recovered particles were washed, dried in a hood and in a vacuum oven (65° C., 0.08 mm Hg) as in Example 1. The resultant zinc dimethacrylate in the form of a lightly caked powder was then broken up in a Waring blender and passed through a 50 mesh screen.

A sample of the product was analyzed and found to contain 33.6% ash.

This example was repeated several times and the product from each run was combined. A sample of product from the combined runs was evaluated and found to have a nitrogen surface area of 4.5 $m^2/g$ and a calculated particle size of 0.78 microns (see Explanatory Note). Nitrogen surface area was determined substantially in accordance with the procedure set forth in ASTM D3037, Method D which is titled: "Surface Area By Monosorb Analyzer" with the significant exception that a degas temperature of 100° C. was used instead of the 200° C. degas temperature specified in the test (see Explanatory Note).

Explanatory Note: The above example corresponds to Example 3 of application Ser. No. 421,012, the parent application of this application. In Example 3 of the parent, the nitrogen surface area is reported as 2.44 $m^2/g$ and the calculated particle size is reported as 1.45 microns. The reason for the discrepancy is that in Example 3 of the parent the exact procedure of ASTM D3037, Method D, which was initially developed to measure the surface area of carbon black and includes a 200° C. degas temperature was utilized. However, since the filing of the parent application, the applicants have discovered that the 200° C. degas temperature causes a disruption of the surface area of zinc dimethacrylate powder thereby resulting in lower surface area values than are actual. However, the above results represent a retesting of the zinc dimethacrylate powder using the modified procedure.

EXAMPLE 4

To a 1-liter beaker equipped with a stirrer and thermometer was charged 391 mililiters (ml) of hexane, 0.11 ml each of Triton X-15, Triton X-45 and Triton X-100 and 32.8 grams of zinc oxide. (Triton X-15, X-45 and X-100 are nonionic octylphenoxy polyethoxy ethanol surfactants available from Rohm & Haas Company). The mixture was stirred for 5 minutes and 67.2 grams of methacrylic acid were then added to the beaker. Following this addition, stirring of the reaction mixture was continued for 23 hours with the temperature being less than 35° C. The resultant fluid suspension was filtered to recover the zinc dimethacrylate particles which were then pressed as dry as possible and air dried overnight. Final drying of the resultant zinc dimethacrylate powder was conducted in a vacuum oven at 60° C.

A sample of the zinc dimethacrylate powder obtained showed a nitrogen surface area of 5.35 $m^2/g$. Nitrogen surface area was determined in accordance with the modified ASTM D3037, Method D, procedure utilized in Example 3 (i.e., 100° C. degas temperature).

EXAMPLE 5

In this example, Example 4 was substantially repeated except that additional agitation was provided using ultrasound.

A sample of the resultant zinc dimethacrylate powder showed a nitrogen surface area of 4.98 $m^2/g$ using the modified surface area procedures of Examples 3 and 4.

COMPARATIVE EXAMPLE A

In this example, the procedure of Chem Abstract Article 87-5403—Kobayashi et al. (Japanese Kokai No. 76,138,616), one of the principal references cited against U.S. application Ser. No. 421,012, the parent application to the present application, was evaluated.

The procedure employed to avaluate the Kobayashi et al. process was as follows:

To a 1-liter flask equipped with stirrer and azeotrope trap with reflux condenser was charged 391 ml toluene and 32.8 grams of zinc oxide. The contents of the flask were stirred and warmed to about 50° C. and then 67.2 grams of methacrylic acid were added. A house vacuum line was attached through the top of the condenser and enough vacuum was applied to cause gentle refluxing. Reaction was terminated after 7 hours at 50° C. when no more water was collected in the azeotrope trays. The contents of the flask were then filtered, the precipitate pressed as dry as possible and air dried overnight. Final drying was conducted in a vacuum oven at 60° C.

The resultant zinc dimethacrylate in the form of a fine white powder had a nitrogen surface area of 3.1 m²/g as determined by the nitrogen surface area procedure of Examples 3-5.

COMPARATIVE EXAMPLES B & C

In these examples, the effects of a zinc dimethacrylate powder produced by the method of the invention (Example 4) and zinc dimethacrylate powder produced by the method of Kobayashi et al. (Example A) on the properties of a vulcanized synthetic rubber composition were evaluated.

The synthetic compositions employed to conduct the evaluations had the following formulations:

|  | parts by weight Example | |
|---|---|---|
|  | B | C |
| S1502[a] | 100.0 | 100.0 |
| Zinc Dimethacrylate of Ex. A | 40.0 | — |
| Zinc Dimethacrylate of Ex. 4 | — | 40.0 |
| Vulcup R[b] | 0.3 | 0.3 |
| Polygard[c] | 2.0 | 2.0 |
| Total | 142.3 | 142.3 |

[a] a styrene/butadiene rubber containing 23.5% bound styrene available from The Firestone Tire & Rubber Company.
[b] bis-(t-butylperoxy)diisopropyl benzene.
[c] a tri-(nonylated phenol) phosphate antioxidant available from Uniroyal.

The above formulations were mixed on a cold two roll mill. The mixed compounds were then cured and tested for stress-strain properties. A visual examination of samples of the cured compounds revealed that the compound of Example B (zinc dimethacrylate of Kobayashi, et al.) was nearly opaque while that of Example C (zinc dimethacrylate of the invention) was almost transparent. Test conditions and results are shown in the table.

TABLE

|  | Example | |
|---|---|---|
|  | B | C |
| Cure time (min) at temp. °C. | 20' at 160° C. | 20' at 160° C. |
| Stress-strain at 23° C. | | |
| 10% modulus, MPa | 1.2 | 1.6 |
| 100% modulus, MPa | 5.8 | 7.5 |
| 200% modulus, MPa | 11.3 | 14.2 |
| Tensile, MPa | 12.8 | 15.1 |
| Elongation at break, % | 226 | 215 |

As can be seen from the above data, the vulcanized polymeric composition of Example C which contains zinc dimethacrylate produced by the method of the invention has much better stress-strain properties than Example B which contains zinc dimethacrylate produced by the method of Kobayashi et al. EXAMPLES 6-8

In these examples, vulcanizable polymeric compositions containing zinc dimethacrylate produced in accordance with the procedures of Examples 1-3 were prepared. Composition formulations were as follows:

| Ingredients | Ex. No. | | |
|---|---|---|---|
|  | 6 | 7 | 8 |
| Hevea (NR) | 100.0 | 100.0 | 100.0 |
| Zinc dimethacrylate | 50.0[1] | 50.0[2] | 50.0[3] |
| Vulcup R[4] | 1.0 | 1.0 | 1.0 |
|  | 151.0 | 151.0 | 151.0 |

[1] prepared in accordance with the procedure of Example 1
[2] prepared in accordance with the procedure of Example 2
[3] prepared in accordance with the procedure of Example 3
[4] bis-(t-butyl peroxy)diisopropyl benzene The above formulations were mixed on an electric mill with no external heat added. The mixed formulations were cured and tested for stress-strain properties. Test conditions and properties are shown in Table I.

TABLE I

|  | Ex. No. | | |
|---|---|---|---|
|  | 6 | 7 | 8 |
| Cure time (min.) at temp. °C. | 20' at 160° C. | 20' at 160° C. | 20' at 160° C. |
| Stress-strain at 23° C. | | | |
| 10% modulus, MPa | 2.5 | 3.4 | 2.7 |
| 300% modulus, MPa | 14.6 | 17.1 | 18.2 |
| Tensile, MPa | 30.1 | 23.8 | 25.5 |
| Elongation at Break | 640 | 446 | 443 |

As will be evident from the above data, vulcanizable polymeric compositions of the invention containing zinc dimethacrylate produced by the method of the invention exhibit excellent 300% modulus and tensile values.

COMPARATIVE EXAMPLES D & E

For comparative purposes, vulcanizable polymeric compositions, having basically the same formulations as in Examples 6-8, were prepared except that a commercially available zinc diemthacrylate was substituted for the zinc dimethacrylate prepared in accordance with the method of the invention. This commercial zinc dimethacrylate was designated MPL #7742 and was commercially available from Monomer Polymer Laboratories. This zinc dimethacrylate prior to use was vacuum dried to an ash content of 34.9% and then evaluated for nitrogen surface area in accordance with the modified ASTM D3037-78, Method D, procedure used in Examples 3-5. The nitrogen surface area of MPL #7742 by the modified procedure was 0.960 m²/g. (Note: these examples correspond to Examples A and B of the parent application and the surface area of MPL #7742 reported therein was 0.73 m²/g by the original ASTM D3037-78, Method D procedure. Hence the above 0.960 m²/g surface area value represents a retest of MPL #7742.)

Two formulations containing MPL #7742 were prepared at different times and tested for stress-strain properties. Compositional formulations designated Examples D and E and test results are shown in Table I(a). For convenience in comparing the stress-strain properties to those obtained by compositions of the invention, a vulcanizable polymeric composition of the invention designated Control, previously prepared and tested, is also included in the Table.

TABLE I(a)

| Ingredients | Control | D | E |
|---|---|---|---|
| Hevea (NR) | 100.0 | 100.0 | 100.0 |
| Zinc dimethacrylate source | Ex. 1 | MPL #7742 | MPL #7742 |
| amount | 50.0 | 50.0 | 50.0 |
| Vulcup R | 1.0 | 1.0 | 1.0 |
| Total | 151.0 | 151.0 | 151.0 |
| Cure time (min.) at temp. °C. | 20' at 160° C. | 20' at 160° C. | 20' at 160° C. |
| Stress-strain at 23° C. | | | |
| 10% modulus, MPa | 2.15 | 0.20 | 0.28 |
| 300% modulus, MPa | 14.10 | 4.10 | 4.96 |
| Tensile, MPa | 23.80 | 13.40 | 13.34 |
| Elongation at Break | 519 | 770 | 692 |

As can be seen from the above data, the compositions containing the MPL #7742 zinc dimethacrylate (nitrogen surface area 0.960) exhibit dramatically lower modulus and tensile values than the Control example or Examples 6–8. Note particularly the difference between the modulus and tensile values of Examples D and E and Example 8 which contains zinc dimethacrylate having a nitrogen surface area of 4.5 m²/g.

The following examples, (i.e., 9–35) further illustrate vulcanizable compositions of the invention containing zinc dimethacrylate prepared by the process of Example 1.

EXAMPLES 9–14

In these examples, vulcanizable polymeric compositions containing various rubbery polymers were prepared. Composition formulations were as follows:

| | Parts by Weight | | | | | |
|---|---|---|---|---|---|---|
| | Example No. | | | | | |
| Ingredients | 9 | 10 | 11 | 12 | 13 | 14 |
| EPDM(a) | 100.0 | — | — | — | — | — |
| FRN510(b) | — | 100.0 | — | — | — | — |
| Hevea (NR) | — | — | 100.0 | — | — | — |
| Neoprene GN | — | — | — | 100.0 | — | — |
| S1502(c) | — | — | — | — | 100.0 | — |
| EPR(d) | — | — | — | — | — | 100.0 |
| Zinc dimethacrylate | 50.0 | 50.0 | 50.0 | 50.0 | 50.0 | 50.0 |
| Vulcup R(e) | 1.0 | 1.0 | 1.0 | 1.0 | 1.0 | 1.0 |

| | Parts by Weight | | | | | |
|---|---|---|---|---|---|---|
| | Example No. | | | | | |
| Ingredients | 9 | 10 | 11 | 12 | 13 | 14 |
| Total | 151.0 | 151.0 | 151.0 | 151.0 | 151.0 | 151.0 |

(a) an ethylene/propylene/diene terpolymer having a Mooney viscosity, ML₄/257° F., of 55 available from Copolymer Corporation under the designation EPSyn 55.
(b) a nitrile rubber containing 32% acrylonitrile.
(c) a styrene/butadiene rubber containing 23.5% bound styrene available from The Firestone Tire & Rubber Company.
(d) a saturated ethylene/propylene rubber available from the B. F. Goodrich Company under the designation EPCAR306.
(e) bis-(t-butyl peroxy)diisopropyl benzene.

The above formulations were mixed on an electric mill with no external heat added. The mixed formulations were cured and then tested for stress-strain properties. Test conditions and properties are shown in Table II.

TABLE II

| | Example No. | | | | | |
|---|---|---|---|---|---|---|
| | 9 | 10 | 11 | 12 | 13 | 14 |
| Cure time (min.) at temp. °C. | 15' at 160° C. | 15' at 160° C. | 15' at 160° C. | 15' at 160° C. | 15' at 160° C. | 30' at 160° C. |
| Stress-strain at 23° C. | | | | | | |
| 10% modulus, MPa | 1.6 | 3.7 | 1.4 | 2.2 | 5.1 | 1.5 |
| 200% modulus, MPa | — | 19.1 | — | — | 24.6 | — |
| 300% modulus, MPa | 10.0 | — | 8.9 | 11.5 | — | 9.8 |
| Tensile, MPa | 23.2 | 19.8 | 20.2 | 16.3 | 24.4 | 17.1 |
| Elongation at Break, % | 615 | 210 | 600 | 460 | 195 | 447 |
| Stress-strain at 100° C. | | | | | | |
| 10% modulus, MPa | 2.1 | — | 1.5 | 2.3 | 3.6 | — |
| 200% modulus, MPa | — | — | — | — | — | — |
| 300% modulus, MPa | 11.5 | — | 7.2 | 11.8 | — | — |
| Tensile, MPa | 17.3 | — | 16.7 | 12.5 | 14.4 | — |
| Elongation at Break, % | 479 | — | 720 | 330 | 150 | — |

As the above data illustrates, vulcanizable polymeric compositions of the invention exhibit high modulus, tensile and elongation when cured. In comparison, a conventional sulfur-curable rubber compound containing a solution styrene/butadiene copolymer having 18% bound styrene, 37.5 parts extender oil, 63 parts HAF black, 1.8 parts sulfur and 2.1 parts of a sulfenamide-type accelerator on curing tested at room temperature has a 10% modulus of 0.44 MPa, a 300% modulus of 6.1 MPa, a tensile of 18.4 MPa, and an elongation at break of 738%.

EXAMPLES 15–18

In these examples, vulcanizable polymeric compositions containing blends of rubbery polymers were prepared. Composition formulations were as follows:

| | Parts by Weight | | | |
|---|---|---|---|---|
| | Example No. | | | |
| Ingredients | 15 | 16 | 17 | 18 |
| Hevea (NR) | 50.0 | 50.0 | — | — |
| EPDM* | 50.0 | — | 50.0 | 50.0 |
| S1502 | — | 50.0 | 50.0 | — |
| FRN510 | — | — | — | 50.0 |
| Zinc dimethacrylate | 50.0 | 50.0 | 50.0 | 50.0 |
| Vulcup R | 1.0 | 1.0 | 1.0 | 1.0 |
| Total | 151.0 | 151.0 | 151.0 | 151.0 |

*EPDM of Example 9.

The above formulations were mixed, cured and tested for stress-strain properties in accordance with the procedure of Examples 6-8. Test conditions and properties are shown in Table III.

TABLE III

|  | Example No. | | | |
|---|---|---|---|---|
|  | 15 | 16 | 17 | 18 |
| Cure | 15' at 160° C. | 15' at 160° C. | 15' at 160° C. | 15' at 160° C. |
| Stress-strain at 25° C. | | | | |
| 10% modulus, MPa | 2.8 | 2.7 | 4.2 | 2.4 |
| 200% modulus, MPa | — | — | 16.7 | — |
| 300% modulus, MPa | 10.2 | 17.7 | — | 9.0 |
| Tensile, MPa | 21.4 | 21.0 | 17.2 | 18.3 |
| Elongation at Break, % | 660 | 360 | 208 | 629 |
| Stress-strain at 100° C. | | | | |
| 10% modulus, MPa | 1.7 | 2.3 | 3.0 | 1.7 |
| 200% modulus, MPa | — | — | — | — |
| 300% modulus, MPa | 6.0 | 12.2 | — | 7.0 |
| Tensile, MPa | 9.5 | 12.2 | 9.2 | 8.7 |
| Elongation at Break, % | 543 | 298 | 119 | 393 |

The above data indicates that the compositions containing blends of rubbery polymers are well cured and exhibit excellent strength. Of particular interest, the composition containing the blend of EPDM and nitrile rubber (Example 18) polymers which are normally incompatible, also cured well and exhibited good properties.

EXAMPLES 19-24

In these examples, vulcanizable polymeric compositions containing variable quantities of zinc dimethacrylate were prepared. Composition formulations were as follows:

|  | Parts by Weight | | | | | |
|---|---|---|---|---|---|---|
|  | Example No. | | | | | |
| Ingredients | 19 | 20 | 21 | 22 | 23 | 24 |
| S1502 | 100.0 | — | — | — | — | — |
| Natural rubber (pale crepe) | — | 100.0 | 100.0 | — | — | — |
| EPDM* | — | — | — | 100.0 | 100.0 | 100.0 |
| Zinc dimethacrylate | 30.0 | 60.0 | 70.0 | 60.0 | 70.0 | 80.0 |
| Vulcup R | 1.0 | 1.0 | 1.0 | 1.0 | 1.0 | 1.0 |
| Total | 131.0 | 161.0 | 171.0 | 161.0 | 171.0 | 181.0 |

*An ethylene/propylene diene terpolymer having a Mooney viscosity of $ML_4/257$ F. of 40 available from Copolymer Corporation under the designation EPSyn 40-A The above formulations were mixed, cured and tested for stress-strain properties in accordance with the procedure of Examples 6-8. Test conditions and properties are shown in Table IV.

TABLE IV

|  | Example No. | | | | | |
|---|---|---|---|---|---|---|
|  | 19 | 20 | 21 | 22 | 23 | 24 |
| Cure | 20' at 160° C. | 15' at 160° C. | 15' at 160° C. | 15' at 160° C. | 15' at 160° C. | 15' at 160° C. |
| Stress-strain at 25° C. | | | | | | |
| 10% modulus, MPa | 0.58 | 3.2 | 4.6 | 2.2 | 3.5 | 4.8 |
| 300% modulus, MPa | 11.1 | 14.6 | 17.2 | 9.8 | 14.0 | 18.7 |
| Tensile, MPa | 13.6 | 26.8 | 25.3 | 25.9 | 27.1 | 25.9 |
| Elongation at Break, % | 349 | 585 | 486 | 747 | 584 | 428 |
| Stress-strain at 100° C. | | | | | | |
| 10% modulus, MPa | — | 2.3 | 3.1 | 1.8 | 2.4 | 3.5 |
| 300% modulus, MPa | — | 8.9 | 10.1 | 7.7 | 9.7 | 12.7 |
| Tensile, MPa | — | 14.6 | 14.0 | 12.7 | 13.0 | 14.9 |
| Elongation at Break, % | — | 568 | 467 | 530 | 426 | 369 |

The room temperature (25° C.) tensile data from Examples 20-24 indicates test compositions containing high levels (e.g., 60-80 parts) of zinc dimethacrylate have tensile strengths (i.e., 25.3-27.1 MPa) approaching those of some commercial polyurethanes. For example, a polyurethane composition composed of Adiprene L-367, a polyurethane prepolymer available from duPont, and Caytur 21 a salt complex of methylene dinanaline available from duPont, when cured for 1 hour at 120° C. exhibits a tensile strength at 25° C. of 27.8 MPa.

EXAMPLES 25-27

In these examples, vulcanizable polymeric compositions containing varying amounts of peroxide curing agents were prepared. Composition formulations were as follows:

|  | Parts by Weight | | |
|---|---|---|---|
|  | Example No. | | |
| Ingredients | 25 | 26 | 27 |
| S1502 | 100.0 | 100.0 | 100.0 |
| Zinc dimethacrylate | 50.0 | 50.0 | 50.0 |
| Vulcup R | 1.0 | 0.5 | 0.2 |
| Total | 151.0 | 150.05 | 150.02 |

The above formulations were mixed, cured and tested for stress-strain properties as in Examples 6-8. Test conditions and properties are shown in Table V.

TABLE V

| Example No. | Cure at 160° C. Time (min.) | Stress-strain (MPa) | | | Elongation % |
|---|---|---|---|---|---|
|  |  | 10% mod | 300% mod | Tensile |  |
| 25 | 10' | 5.0 | — | 21.5 | 165 |
|  | 20 | 8.4 | — | 13.5 | 36 |

TABLE V-continued

| Example No. | Cure at 160° C. Time (min.) | Stress-strain (MPa) 10% mod | 300% mod | Tensile | Elongation % |
|---|---|---|---|---|---|
| 26 | 10 | 3.0 | 19.0 | 20.1 | 322 |
|    | 20 | 5.2 | —    | 19.5 | 138 |
| 27 | 20 | 3.0 | 19.7 | 21.9 | 345 |
|    | 30 | 3.6 | 23.8 | 22.2 | 278 |

EXAMPLES 28–31

In these examples, vulcanizable polymeric compositions containing added reinforcing fillers were prepared. Composition formulations were as follows:

| | Parts by Weight | | | |
|---|---|---|---|---|
| | Example No. | | | |
| Ingredients | 28 | 29 | 30 | 31 |
| S1502 | 100.0 | 100.0 | — | — |
| Natural rubber | — | — | 100.0 | 100.0 |
| Zinc diamethacrylate | 65.0 | 37.5 | 65.0 | 50.0 |
| HAF black | 5.0 | 12.5 | 5.0 | 25.0 |
| Vulcup R | 0.2 | 0.2 | 1.0 | 1.0 |
| Total | 170.2 | 150.2 | 171.0 | 176.0 |

The above formulations were mixed on a mill, cured and tested for stress-strain properties. Cure conditions, test conditions and properties are shown in Table VI.

TABLE VI

| | Example No. | | | |
|---|---|---|---|---|
| | 28 | 29 | 30 | 31 |
| Cure | 20′ at 160° C. | 20′ at 160° C. | 30′ at 160° C. | 30′ at 160° C. |
| Stress-strain at 25° C. | | | | |
| 10% modulus, MPa | 3.2 | 1.1 | 3.8 | 3.0 |
| 300% modulus, MPa | 15.7 | 9.0 | 22.4 | 20.6 |
| Tensile, MPa | 19.1 | 20.2 | 22.2 | 22.5 |
| Elongation at Break, % | 398 | 721 | 301 | 339 |

EXAMPLES 32–35

In these examples, vulcanizable polymeric compositions containing 50 parts HAF and variable quantities of zinc dimethacrylate were prepared. The effect of zinc dimethyacrylate on hysteresis properties was evaluated using a conventional shear modulus test. In the shear modulus test, G′ represents shear modulus, G″ represents shear modulus loss and Tan is the ratio of shear modulus to shear modulus loss. Tan is regarded as an indication of hysteresis properties with low values indicating lower hysteresis and higher values indicating higher hysteresis. The compositions were mixed on a mill and cured and evaluated for shear modulus at low strain. Composition formulations, cure conditions, test conditions and shear modulus results are shown in Table VII.

TABLE VII

| | Example No. | | | |
|---|---|---|---|---|
| Ingredients | 32 | 33 | 34 | 35 |
| S1502 | 100.0 | 100.0 | 100.0 | 100.0 |
| HAF black | 50.0 | 50.0 | 50.0 | 50.0 |
| Zinc dimethacrylate | 50.0 | 40.0 | 30.0 | 20.0 |
| Vulcup R | 0.2 | 0.2 | 0.2 | 0.2 |
| Total | 200.2 | 190.2 | 180.2 | 170.2 |
| Cure at 160° C. (min.) | 30 | 30 | 30 | 30 |
| Test temperature, °C. | 75 | 75 | 75 | 75 |
| Shear Modulus | | | | |
| 10% strain, G′ Mpa | 4.14 | 3.49 | 2.64 | 1.64 |
| G″ | 0.69 | 0.59 | 0.46 | 0.32 |
| Tan | 0.168 | 0.169 | 0.174 | 0.195 |

The above data indicates that with increasing amounts of zinc dimethacrylate at constant black loading, the modulus of the compound significantly increases while the Tan values are decreasing. This would appear to indicate a lower hysteresis property at higher modulus which is an unusual and unexpected result.

We claim

1. A method of preparing a zinc dimethacrylate powder having a surface area of from about 3.7 to about 5.4 m$^2$/g which comprises:
    (a) reacting under agitation zinc oxide and methacrylic acid in an amount of from about 0.5 to about 0.6 moles of zinc oxide per mole of methacrylic acid in a liquid aliphatic hydrocarbon dispersing medium to produce particles of zinc dimethyacrylate in the liquid medium;
    (b) recovering said particles of zinc dimethacrylate from said liquid medium by filtration or evaporation of the liquid medium; and
    (c) drying said particles of zinc dimethacrylate to produce said zinc dimethacrylate powder.

2. The method of claim 1 further comprising the steps comprising the steps of breaking up the powder and passing it through a sieve.

3. The method of claim 1 wherein the zinc oxide and methacrylic acid are reacted at room temperature.

4. The method of claim 1 wherein a nonionic surfactant is included in the liquid aliphatic hydrocarbon dispersing medium.

5. The method of claim 4 wherein the nonionic surfactant is an alkylaryl polyether alcohol.

6. The method of claim 1 wherein the liquid aliphatic hydrocarbon is hexane.

* * * * *